United States Patent [19]

Biere et al.

[11] 3,965,103

[45] June 22, 1976

[54] 4-NITROPERHYDROPYRIDO[1,2-A][1,4]DIAZEPINES

[75] Inventors: Helmut Biere; Hermann Ulbrich; Hans-Joachim Kessler; Ulrich Redmann, all of Berlin, Germany

[73] Assignee: Schering Aktiengesellschaft, Berlin & Bergkamen, Germany

[22] Filed: Sept. 20, 1974

[21] Appl. No.: 507,684

[30] Foreign Application Priority Data

Sept. 20, 1973  Germany............................ 2347886

[52] U.S. Cl............................. 260/293.55; 424/267
[51] Int. Cl.[2]....................................... C07D 471/02
[58] Field of Search................................ 260/293.55

[56] References Cited
UNITED STATES PATENTS 3,531,485   9/1970   Freed................................. 260/268

Primary Examiner—G. Thomas Todd
Attorney, Agent, or Firm—Millen, Raptes & White

[57] ABSTRACT

Compounds of the formula

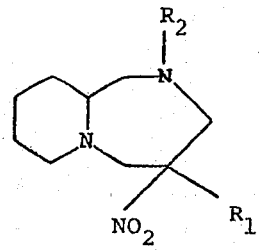

wherein $R_1$ is H, lower-alkyl, hydroxyalkyl, phenyl, aralkyl, or —$(CH_2)_n$—X wherein $n$ is 0–4 and X is —COO-lower-alkyl, C ≡ N or —COOH and $R_2$ is H, lower-alkyl or aralkyl, produced by condensing a diamine of the formula

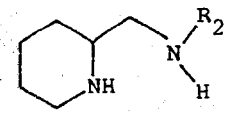

with a nitro compound of the formula $R_1$—$CH_2$—$NO_2$ in the presence of formalin or paraformaldehyde, or with the $R_1$—$C(CH_2OH)_2NO_2$ reaction product of the above nitro compound and formalin or paraformaldehyde, or with formalin or paraformaldehyde followed by reaction with the above nitro compound, and their acid addition salts, possess antimicrobial activity against both gram-positive and gram-negative bacteria and also against dermatophytes, yeasts and other fungi.

27 Claims, No Drawings

4-NITROPERHYDROPYRIDO[1,2-A][1,4]DIAZEPINES

BACKGROUND OF THE INVENTION

This invention relates to novel heterocyclic nitro compounds and processes for the production thereof.

It is known from U.S. Pat. No. 3,558,788 that 2-bromo-2-nitropropane-1,3-diol ("Bronopol") has antibacterial activity. The nitro compounds of this invention have improved properties as compared to this compound, and exhibit, with equal effectiveness against gram-positive and gram-negative bacteria, greater activity against dermatophytes, yeasts and other fungi.

SUMMARY OF THE INVENTION

In a composition aspect, this invention relates to compounds of general Formula I

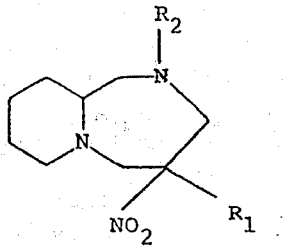

I wherein $R_1$ is a hydrogen atom, straight or branched alkyl of 1–12 carbon atoms, phenyl, aralkyl of 7–10 carbon atoms, hydroxyalkyl of 1–4 carbon atoms, or —$(CH_2)_n$—X wherein $n$ is an integer from 0–4, inclusive, and X is alkoxycarbonyl of 1–4 carbon atoms in the alkoxy group, nitrile, or carboxy and $R_2$ is a hydrogen atom, alkyl of 1–4 carbon atoms, aralkyl of 7–10 carbon atoms, and the pharmaceutically acceptable acid addition salts thereof with physiologically acceptable acids, both in the form of the racemates and their optically active antipodes.

DETAILED DISCUSSION

Examples of alkyl of 1–4 carbon atoms are methyl, ethyl, n-propyl, isopropyl, n-butyl and isobutyl, preferably methyl. Examples of hydroxyalkyl and alkoxy groups are the corresponding groups bearing an OH and an —O— group, respectively, preferably on the α— or β— carbon atom, e.g., hydroxymethyl, β-hydroxyethyl, methoxy and ethoxy. Alkyl of 1–12 carbon atoms include additionally amyl, n-hexyl, n-heptyl, n-octyl, n-decyl, n-undecyl, n-dodecyl and the branched chain isomers thereof.

Examples of —$(CH_2)_n$—X groups are carboxy, cyano, carbomethoxy, carboethoxy and methylene, ethylene, trimethylene, α-methyl- and β-methylethylene bearing one of the above groups, e.g., cyanomethyl, cyanoethyl, methoxycarbonylethyl.

Examples of arylalkyl are monocyclic carbocyclic aralkyl having a benzene ring joined to an alkyl group of 1–4 carbon atoms, e.g., benzyl, phenethyl, γ-phenylpropyl, α-xylyl and p-tolylethyl.

Examples of physiologically acceptable acids for forming the salts are hydrochloric acid, sulfuric acid, nitric acid, phosphoric acid, acetic acid, propionic acid, lactic acid, succinic acid, tartaric acid, citric acid, benzoic acid, salicylic acid, nicotinic acid and heptagluconic acid.

In its process aspect, this invention relates to a process for the production of the compounds of general Formula I, which comprises a. condensing a diamine of general Formula II

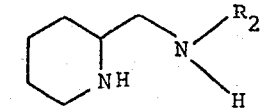

II wherein $R_2$ has the values given above with a nitro compound of general Formula III $R_1 — CH_2 — NO_2$     III wherein $R_1$ has the values given above, in the presence of formalin or paraformaldehyde; or b. reacting a nitro compound of general Formula III with paraformaldehyde or formalin in the presence of a basic catalyst to produce a bis(hydroxymethyl)nitro compound of the general Formula IV

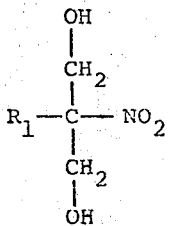

IV and then condensing the latter with a diamine of the general Formula II; or c. reacting a diamine of general Formula II with formalin or paraformaldehyde and then cyclizing the product with a nitro compound of general Formula III; and optionally thereafter converting a compound obtained according to any of steps (a), (b) or (c) in a conventional manner with a physiologically compatible acid into an acid addition salt thereof.

Compounds of Formula I wherein $R_2$ is a hydrogen atom can be prepared from the corresponding 2-benzyl compounds by selective reductive cleavage of the benzyl group in the conventional manner.

Reactions (a), (b) and (c) can be conducted in aqueous media (40% formaldehyde solution), or in an anhydrous solvent, for example, an alcohol or an ether, e.g., dioxane, tetrahydrofuran, dimethoxyethane, etc., employing paraformaldehyde.

The reaction can be conducted over a wide temperature range, viz., 0–100° C. Preferably, the exothermic reactions are first controlled by cooling, and the reaction mixture is heated toward the end of the reaction, preferably to 60°–80° C.

In reaction (b), suitable as basic catalysts are both inorganic and organic bases, e.g, potassium carbonate, sodium alcoholate, alkali hydroxides and quaternary organic amines, e.g., "Triton B" (benzyltrimethylammonium hydroxide).

Due to their broad antimicrobial spectrum of activity and their low toxicity, the compounds of this invention are especially suitable for use as preservatives but also as antimicrobial compositions for topical therapy or as antimicrobial additives to pharmaceutical compositions which are applicable in external therapy against bacteria and fungi, where they are generally employed at concentrations of from 0.005 to 1%, preferably from 0.01 to 0.1% by weight.

The above mentioned greater activity against dermatophytes, yeasts and other fungi compared to "Bronopol" is illustrated in Table 1:

TABLE 1

| | MIC ($\mu$g./ml.) in the Tube Dilution Test in liquid media | | |
|---|---|---|---|
| | "Bronopol" 2-Bromo-2-nitropropane-1,3-diol | 4-n-Butyl-2-methyl-4-nitroperhydropyrido[1,2-a][1,4]diazepine dihydrochloride | 4-Benzyl-2-methyl-4-nitroperhydropyrido[1,2-a][1,4]diazepine dihydrochloride |
| Candid. alb. | 63 | 8 | 4 |
| Sacch. cer. | 125 | 4 | 4 |
| Trichoph. ment. | 8 | 2 | 4 |
| Trichoph. rubr. | 4 | 2 | 2 |
| Microsp. gypseum | 16 | 8 | 8 |
| Asp. fum. | 63 | 8 | 31 |
| Asp. flav. | >1000 | 4 | 63 |
| Asp. nig. | >1000 | 31 | 125 |
| Pen. notat. | >1000 | 8 | 125 |
| Mucor. pus. | 63 | 2 | 8 |
| Fusar. | 250 | 16 | 63 |
| Paecilomyc. | 250 | 63 | 16 |
| Chaet. glob. | >1000 | 8 | 63 |

Due to their broad spectrum of activity the compounds of this invention are useful as preservatives and additives in pharmaceutical compositions and as valuable chemotherapeutic agents against fungi and dermatophytes in the human and veterinary medicine.

The novel compounds of this invention can be employed as preservatives and stabilizers in admixture with conventional pharmaceutical excipients. Carrier substances can be such organic or inorganic substances suitable for topical application such as, for example, water, vegetable oils, polyethylene glycols, gelatine, vaseline, paraffin oil, talcum, ceresine, perfume oil, wool fat, white wax, etc. The novel compounds can be combined with other active substances suitable for topical application, for example corticoids, such as fluocortolone and fluocortolone esters.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1 a. 2,4-Dimethyl-4-nitroperhydropyrido[1,2-a] [1,4]diazepine 1.2 g. of paraformaldehyde is suspended in 10 ml. of methanol and agitated with 1.5 g. of nitroethane at room temperature for 30 minutes. Thereafter, 2.6 g. of α-(methylamino)-pipecoline is added dropwise, and after the addition of the amine is finished, the bath temperature is set at 50° C. After the paraformaldehyde is completely dissolved, the solvent is withdrawn under vacuum, the residue is taken up in cyclohexane, and filtered over aluminum oxide (neutral). After concentration, 3.0 g. (67% of theory) of a colorless oil is obtained ($n_D^{20}$ = 1.4960).

b. 2,4-Dimethyl-4-nitroperhydropyrido[1,2-a] [1,4]diazepine dihydrochloride

Under agitation, a solution of 2.27 g. of 2,4-dimethyl-4-nitroperhydropyrido[1,2-a][1,4]diazepine in 10 ml. of ethyl acetate is added to 20 ml. of 2N ethereal hydrochloric acid. The residue remaining after concentration is crystallized from chloroform; m.p. 189° C.

EXAMPLE 2

2,4-Dimethyl-4-nitroperhydropyrido[1,2-a] [1,4]diazepine dihydrochloride 11.3 g. of aqueous 40% formalin solution is combined under ice cooling with a mixture of 7.6 g. of α-(methylamino)-pipecoline, as well as 4.5 g. of nitroethane and thereafter stirred for 24 hours at room temperature. The mixture is then combined with ethyl acetate and washed with potassium carbonate solution. After concentration of the organic phase, the residue is mixed with cyclohexane and chromatographed over aluminum oxide (neutral).

The thus-obtained oil is converted into the dihydrochloride as set forth in Example 1(b). Yield: 9.5 g. (53% of theory); m.p. 188° C.

EXAMPLE 3

4-Ethyl-2-methyl-4-nitroperhydropyrido[1,2-a] [1,4]diazepine dihydrochloride

This compound is produced analogously to Example 2 with 1-nitropropane. Yield: 40% m.p. 197° C. (acetone).

EXAMPLE 4

4-n-Butyl-2-methyl-4-nitroperhydropyrido[1,2-a] [1,4]diazepine dihydrochloride

This substance is prepared in analogy to Example 1 with 1-nitropentane. Yield: 35%; m.p. 184° C. (methanol/ether).

EXAMPLE 5 a.
4-(2-Methoxycarbonylethyl)-2-methyl-4-nitroperhydropyrido[1,2-a] [1,4]diazepine This compound is prepared as set forth in Example 1(a) with the methyl ester of 4-nitrobutyric acid. Yield: 30%.

b.
4-(2-Methoxycarbonylethyl)-2-methyl-4-nitroperhydropyrido[1,2-a] [1,4]diazepine dihydrochloride This compound is produced analogously to Example 1(b). Melting point: 154° C. (acetone).

EXAMPLE 6

4-(2-Cyanoethyl)-2-methyl-4-nitroperhydropyrido[1,2-a] [1,4]diazepine dihydrochloride This substance is prepared analogously to Example 1 with 4-nitrobutyronitrile.

EXAMPLE 7

2-Methyl-4-nitro-4-n-propylperhydropyrido[1,2-a] [1,4]-diazepine dihydrochloride This compound is prepared analogously to Example 1 from 1-nitrobutane. Melting point: 191° C (methanol-ether)

EXAMPLE 8

4-Isobutyl-2-methyl-4-nitroperhydropyrido[1,2-a] [1,4]-diazepine dihydrochloride This substance is produced in analogy to Example 1 from 2-methyl-4-nitrobutane. Melting point: 182° C (methanol-ether)

EXAMPLE 9

2-Methyl-4-nitro-4-n-pentylperhydropyrido[1,2-a] [1,4]diazepine dihydrochloride

This compound is prepared as described in Example 1 from 1-nitrohexane. Melting point: 184° C (methanol-ether)

EXAMPLE 10

2-Methyl-4-nitro-4-undecylperhydropyrido[1,2-a] [1,4]diazepine dihydrochloride

This compound is prepared analogously to Example 1 from 1-nitrododecane. Melting point: 184° C (methanol-ether)

EXAMPLE 11

2-Methyl-4-nitro-4-phenylperhydropyrido[1,2-a] [1,4]diazepine dihydrochloride

This substance is produced as set forth in Example 1 from phenylnitromethane. dihydrochloride hydrate m.p. 151° C (methanol-ether) free base m.p. 96° C (petrolether)

EXAMPLE 12

2-Benzyl-4-n-butyl-4-nitroperhydropyrido[1,2-a][1,4]diazepine dihydrochloride

This substance is prepared analogously to Example 1 from 1-nitropentane and α-(benzylamino)-pipecoline. m.p. 186° C (methanol-ether) free base m.p. 104° C (ether)

EXAMPLE 13

4-Hydroxymethyl-2-methyl-4-nitroperhydropyrido[1,2-a] [1,4]diazepine hydrochloride 3.0 g. of 1,3-dihydroxy-2-hydroxymethyl-2-nitropropane is dissolved in 10 ml. of methanol and combined, under ice cooling, with 2.5 g. of α-(methylamino)-pipecoline. The solution is agitated for 30 minutes at room temperature and then heated to 60° C for 3 hours. After concentration under vacuum, the residue is filtered over aluminum oxide (neutral), and the thus-obtained product is converted with equimolar amounts of hydrochloric acid into the hydrochloride. Melting point: 161° C. (methanol/ether).

EXAMPLE 14

2-Methyl-4-nitroperhydropyrido[1,2-a] [1,4]diazepine dihydrochloride

This compound is prepared analogously to Example 13 from 2-nitropropane-1,3-diol.

EXAMPLE 15

4-Methoxycarbonyl-2-methyl-4-nitroperhydropyrido[1,2-a] [1,4]diazepine dihydrochloride Under ice cooling, 2.5 g. of α-(methylamino)-pipecoline is added dropwise to 3 ml. of 40% formalin solution, and the mixture is agitated for 2 hours. Thereafter, 2.4 g. of the methyl ester of nitroacetic acid is added thereto and the mixture is maintained for another 3 hours at room temperature. After the solvent has been withdrawn, the residue is suspended in ethyl acetate and precipitated analogously to Example 1(b) as the dihydrochloride.

EXAMPLE 16

4-Benzyl-2-methyl-4-nitroperhydropyrido[1,2-a] [1,4]-diazepine dihydrochloride

This compound is prepared analogously to Example 1 with 2-phenylnitroethane. Melting point 180° C (methanol-ether) free base m.p. 101° (ether)

EXAMPLE 17

4-Hexyl-2-methyl-4-nitroperhydropyrido[1,2-a] [1,4]-diazepine dihydrochloride

This compound is prepared analogously to Example 1 from 1-nitroheptane. Melting point 185° C (methanol-ether)

EXAMPLE 18

4-Heptyl-2-methyl-4-nitroperhydropyrido[1,2-a] [1,4]-diazepine dihydrochloride

This compound is prepared as described in Example 1 from 1-nitrooctane. Melting point 183° C (methanol-ether)

EXAMPLE 19

| | Ointment with antimicrobial effect |
|---|---|
| 3 % | Polyoxyl-40-stearate |
| 10 % | white petrolatum |
| 10 % | mineral oil |
| 8 % | stearyl alcohol |
| 0.1 % | 2-Methyl-4-nitro-4-propylperhydropyrido[1,2-a]-[1,4]diazepine dihydrochloride |
| 68.9 % | demineralized water |

EXAMPLE 20

| | Additive to a pharmaceutical composition |
|---|---|
| 0.25 % | Fluocortolon trimethylester |
| 0.25 % | Fluocortolon capronate |
| 0.1 % | 4-Butyl-2-methyl-4-nitroperhydropyrido-[1,2-a][1,4]diazepine dihydrochloride |
| 5 % | white wax DAB 6 (Deutsches Arzneibuch 6) |
| 5 % | wool fat, anhydrous, DAB 6 |
| 20 % | vaseline, white DAB 6 |
| 25 % | Amphocerin(R)K "Dehydag" |
| 15 % | paraffin oil, liquid DAB 6 |
| 0.02 % | Crematest. Perfume Oil No. 6580 "Dragee" |
| 29.38 % | water, demineralized |

The preceding examples can be repeated with similar success by substituting the generically or specifically described reactants and/or operating conditions of this invention for those used in the preceding examples.

From the foregoing description, one skilled in the art can easily ascertain the essential characteristics of this

What is claimed is:
1. A compound of the formula

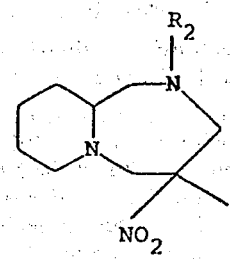

wherein $R_1$ is a hydrogen atom, alkyl of 1—12 carbon atoms, phenyl, hydrocarbon monocycle aralkyl of 7–10 carbon atoms, hydroxyalkyl of 1–4 carbon atoms, or —$(CH_2)_n$—X wherein n is an integer from 0–4, inclusive and X is alkoxycarbonyl of 1–4 carbon atoms in the alkoxy group, nitrile, or carboxy, and $R_2$ is a hydrogen atom, alkyl of 1—4 carbon atoms or hydrocarbon monocyclic aralkyl of 7—10 carbon atoms, or a physiologically acceptable acid addition salt thereof.

2. A compound of claim 1 wherein $R_2$ is benzyl.
3. A compound of claim 1 wherein $R_2$ is methyl.
4. A compound of claim 1 wherein $R_1$ is alkyl of 1–12 carbon atoms.
5. A compound of claim 1 wherein $R_1$ is —$(CH_2)_n$—C≡N wherein n has the values given therein.
6. A compound of claim 1 wherein $R_1$ is —$(CH_2)_n$—CO-alkoxy wherein n has the values given therein and alkoxy is of 1–4 carbon atoms.
7. A compound of claim 1 wherein $R_1$ is —$(CH_2)_n$OH wherein n has the values given therein.
8. A compound of claim 1 wherein $R_1$ is benzyl.
9. 2,4-Dimethyl-4-nitroperhydropyrido[1,2-a][1,4]diazepine, a compound of claim 1.
10. 2,4-Dimethyl-4-nitroperhydropyrido[1,2-a][1,4]diazepine dihydrochloride, a compound of claim 1.
11. 4-Ethyl-2-methyl-4-nitroperhydropyrido[1,2-a][1,4]diazepine dihydrochloride, a compound of claim 1.
12. 4-n-Butyl-2-methyl-4-nitroperhydropyrido[1,2-a][1,4]diazepine dihydrochloride, a compound of claim 1.
13. 4-(2-Methoxycarbonylethyl)-2-methyl-4-nitroperhydropyrido[1,2-a][1,4]diazepine, a compound of claim 1.
14. 4-(2-Methoxycarbonylethyl)-2-methyl-4-nitroperhydropyrido[1,2-a][1,4]diazepine dihydrochloride, a compound of claim 1.
15. 4-(2-Cyanoethyl)-2-methyl-4-nitroperhydropyrido[1,2-a]-[1,4]diazepine dihydrochloride, a compound of claim 1.
16. 2-Methyl-4-nitro-4-n-propylperhydropyrido[1,2-a][1,4]-diazepine dihydrochloride, a compound of claim 1.
17. 4-Isobutyl-2-methyl-4-nitroperhydropyrido [1,2-a][1,4]-diazepine dihydrochloride, a compound of claim 1.
18. 2-Methyl-4-nitro-4-n-pentylperhydropyrido[1,2-a][1,4]-diazepine dihydrochloride, a compound of claim 1.
19. 2-Methyl-4-nitro-4-undecylperhydropyrido[1,2-a][1,4]-diazepine dihydrochloride, a compound of claim 1.
20. 2-Methyl-4-nitro-4-phenylperhydropyrido[1,2-a][1,4]-diazepine dihydrochloride, a compound of claim 1.
21. 2-Benzyl-4-n-butyl-4-nitroperhydropyrido[1,2-a][1,4]-diazepine dihydrochloride, a compound of claim 1.
22. 4-Hydroxymethyl-2-methyl-4-nitroperhydropyrido-[1,2-a][1,4]diazepine hydrochloride, a compound of claim 1.
23. 2-Methyl-4-nitroperhydropyrido[1,2-a][1,4]diazepine dihydrochloride, a compound of claim 1.
24. 4-Methoxycarbonyl-2-methyl-4-nitroperhydropyrido-[1,2-a][1,4]diazepine dihydrochloride, a compound of claim 1.
25. 4-Benzyl-2-methyl-4-nitroperhydropyrido[1,2-a][1,4]-diazepine dihydrochloride, a compound of claim 1.
26. 4-Hexyl-2-methyl-4-nitroperhydropyrido[1,2-a][1,4]-diazepine dihydrochloride, a compound of claim 1.
27. 4-Heptyl-2-methyl-4-nitroperhydropyrido[1,2-a][1,4]-diazepine dihydrochloride, a compound of claim 1.

* * * * *